(12) United States Patent
Liang et al.

(10) Patent No.: US 9,738,909 B1
(45) Date of Patent: Aug. 22, 2017

(54) METHOD OF TRANSFORMING BIOMASS INTO HYDROCARBON

(71) Applicant: Institute of Nuclear Energy Research, Atomic Energy Council, Executive Yuan, R.O.C., Taoyuan (TW)

(72) Inventors: Kuo-Chao Liang, Taoyuan (TW); Feng-Mei Ye, Taoyuan (TW); Cheng-Gang Wu, Taoyuan (TW)

(73) Assignee: INSTITUTE OF NUCLEAR ENERGY RESEARCH, ATOMIC ENERGY COUNCIL, Executive Yuan, R.O.C., Lungtan, Taoyuan (TW)

( * ) Notice: Subject to any disclaimer, the term of this patent is extended or adjusted under 35 U.S.C. 154(b) by 0 days.

(21) Appl. No.: 15/049,272

(22) Filed: Feb. 22, 2016

(51) Int. Cl.
*C12P 5/02* (2006.01)
*C12P 5/00* (2006.01)

(52) U.S. Cl.
CPC ............. *C12P 5/005* (2013.01); *C12P 5/02* (2013.01); *C12P 5/023* (2013.01)

(58) Field of Classification Search
CPC .................................................. C07C 1/24
See application file for complete search history.

(56) References Cited

U.S. PATENT DOCUMENTS

| 8,772,557 B2 * | 7/2014 | Chen | C10L 1/023 585/14 |
|---|---|---|---|
| 2012/0323055 A1 * | 12/2012 | Gruber | C07C 1/24 585/14 |

* cited by examiner

*Primary Examiner* — Bin Shen
(74) *Attorney, Agent, or Firm* — Jackson IPG PLLC; Demian K. Jackson

(57) ABSTRACT

A method is provided to transform biomass. Non-food biomass is preprocessed. Then, fermentation is processed to generate ethanol. Ethanol is dehydrated through a catalyst to generate ethylene. After the dehydration, oligomerization is processed with a catalyst to transform ethylene into olefins having 6~20 carbon atoms ($C_6$~$C_{20}$). The olefins are hydrotreated into alkanes. Thus, $C_6$~$C_{20}$ hydrocarbons having long carbon chains are formed. The hydrocarbons having 6~10 carbon atoms can be used as gasoline; those having 8~16 carbon atoms, jet fuel; and those having 16~20 carbon atoms, diesel. On generating ethanol, byproducts of lignin may be generated. The byproducts can be processed through depolymerization/deoxygenation to generate aromatic hydrocarbons or can be gasified to generate methanol or dimethyl ether. By further processing dehydration, aromatic hydrocarbons are generated to be mixed into gasoline, jet fuel or diesel. Or, the lignin byproducts are gasified to generate syngas.

5 Claims, 1 Drawing Sheet

METHOD OF TRANSFORMING BIOMASS INTO HYDROCARBON

TECHNICAL FIELD OF THE INVENTION

The present invention relates to transforming biomass into hydrocarbons; more particularly, relates to a second-generation bio-ethanol technology for transforming primary products of ethanol into gasoline/jet fuel/diesel and transforming byproducts of lignin into aromatic hydrocarbons/hydrogen, where biomass refining processes are integrated to effectively increase product breadth and reduce production cost.

DESCRIPTION OF THE RELATED ARTSKI

Owing to global climate change and peak oil, alternative energy sources and development of renewable energies are flourished. Yet, aviation fuel is not replaceable by electricity. Intergovernmental Panel on Climate Change (IPCC) noted that, if the aviation industries did not solve the carbon emission problems, their anthropogenic emissions of carbon will reach 15% in 2050. International Air Transport Association (IATA) decided 10% of biomass fuel should be added in aviation fuel in 2017 and carbon emissions made by the airline industries should not increase in 2020. Therefore, the development of renewable aviation fuel has become a top priority.

Currently, technologies related to producing biomass aviation fuel mainly include the following categories:

(1) Fischer-Tropsch Synthesis (FTS): Biomass is used to produce syngas through gasification; and, then, FTS is used for transformation to get liquid hydrocarbons; and, at last, aviation fuel is made through refining.

(2) Hydrotreated Renewable Jet (HRJ): Bio-oil, such as hydrogenated vegetable oil (HVO), is used to produce aviation fuel through hydrodeoxygenation.

However, a disadvantage of FTS is low product selectivity, which needs refining, and is not suitable for small-scale production. Moreover, it has problem on supplying biomass material. Besides, FTS fuel is in lack of aromatic hydrocarbons, which can be partially added only without fully replacing fossil aviation fuel. The disadvantage of HRJ is a narrow product distribution with quite a big difference to existing fossil oils—which raises concern on compatibility. Therefore, HRJ is the same as to be partially added only without fully replacing fossil aviation fuel, not to mention the manufacturing cost is high. There are also technologies of using alcohol to be transformed into biomass aviation fuel, such as the patents applied by Gevo Co. (U.S. Pat. Nos. 8,373,012, 8,378,160, and 8,487,149). But, they concentrates on using butanol as a raw material; or focuses on developing the process of alcohol only.

Hence, the prior arts do not fulfill all users' requests on actual use.

SUMMARY OF THE INVENTION

The main purpose of the present invention is to provide a second-generation bio-ethanol technology for transforming primary products of ethanol into gasoline/jet fuel/diesel and transforming byproducts of lignin into aromatic hydrocarbons/hydrogen, where biomass refining processes are integrated to effectively increase product breadth and reduce production cost.

To achieve the above purpose, the present invention is a method of transforming biomass into hydrocarbons, the method integrating biomass refining processes to transform primary products of ethanol into gasoline/jet fuel/diesel and transform byproducts of lignin into aromatic hydrocarbons/hydrogen, comprising steps of: (a) preprocessing a non-grain biomass and fermenting the biomass into main products of ethanol and byproducts of lignin; processing the products of ethanol through dehydration with a catalyst to obtain products of ethylene; transforming the products of ethylene into products of olefin having 6~20 carbon atoms through oligomerization with a catalyst; and hydrotreating the products of olefin into products of hydrocarbon of alkane having long carbon chains of $C_6$~$C_{20}$, where the products of hydrocarbon having 6~10 carbon atoms are used as gasoline; the products of hydrocarbon having 8~16 carbon atoms are used as jet fuel; and the products of hydrocarbon having 16~20 carbon atoms are used as diesel; and (b) processing the products of lignin through depolymerization/deoxygenation to obtain products of aromatic hydrocarbon; processing the products of lignin through gasification to obtain products of syngas; processing the products of syngas through a synthesis reaction or a water-gas shift reaction, where the products of syngas is processed through the synthesis reaction to generate methanol or dimethyl ether to be dehydrated with a catalyst to generate products of aromatic hydrocarbon to be blended into gasoline/jet fuel/diesel; and where the products of syngas is processed through the water-gas shift reaction to generate hydrogen to be used in hydrogenation reactions of olefins. Accordingly, a novel method of transforming biomass into hydrocarbons is obtained.

BRIEF DESCRIPTION OF THE DRAWING

The present invention will be better understood from the following detailed description of the preferred embodiment according to the present invention, taken in conjunction with the accompanying drawing, in which.

DESCRIPTION OF THE PREFERRED EMBODIMENT

Figure 1:
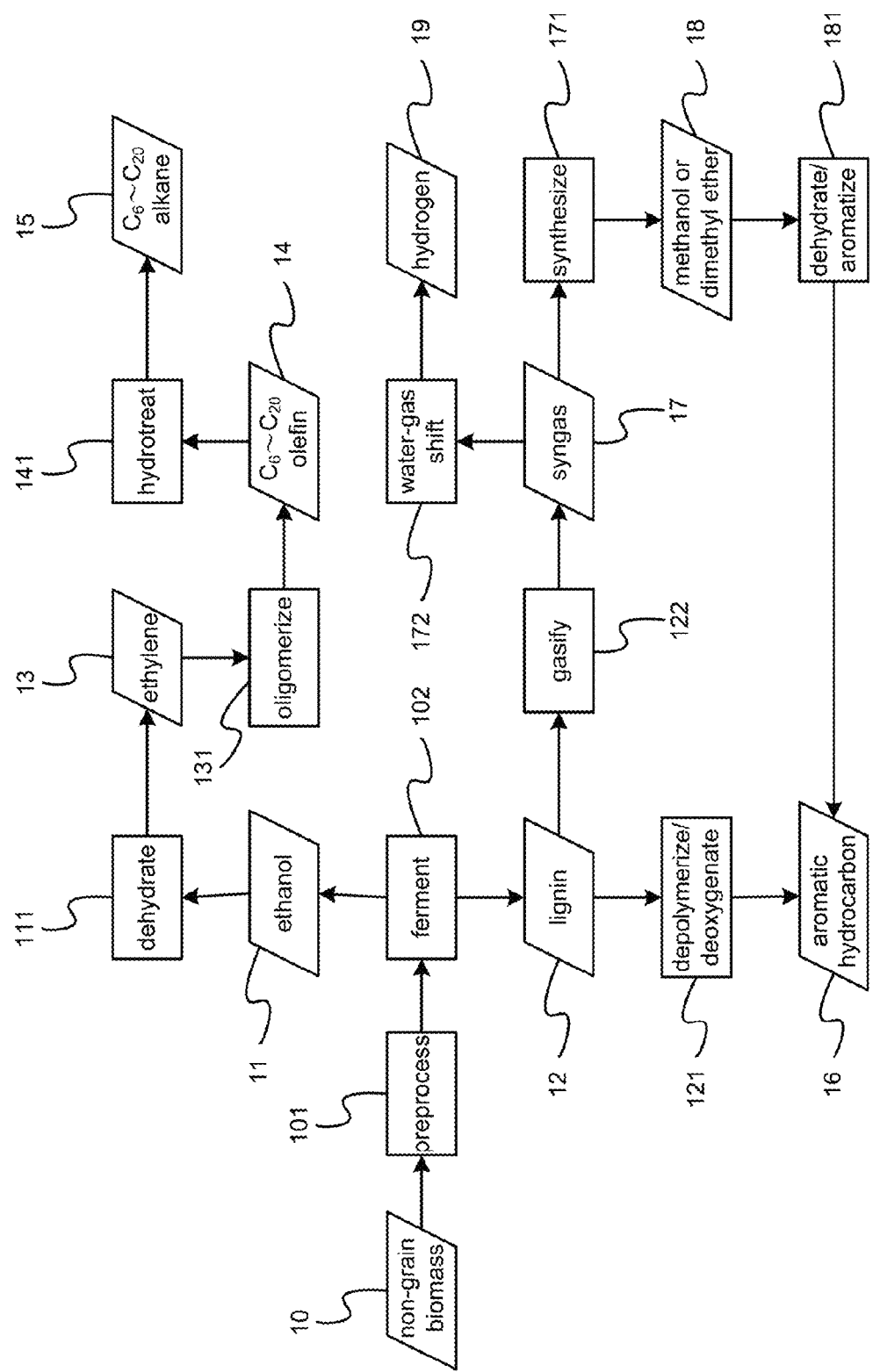
FIG. 1 is the flow view showing the preferred embodiment according to the present invention.

The following description of the preferred embodiment is provided to understand the features and the structures of the present invention.

Please refer to FIG. 1, which is a flow view showing a preferred embodiment according to the present invention. As shown in the FIGURE, the present invention is a method of transforming biomass into hydrocarbons, which integrates biomass refining processes to transform primary products of ethanol into gasoline/jet fuel/diesel and to transform byproducts of lignin into aromatic hydrocarbons/hydrogen, comprising the following steps:

(a) A non-grain biomass 10 is preprocessed 101 and, then, fermented 102 into main products of ethanol 11 and byproducts of lignin 12. The products of ethanol 11 are processed through dehydration 111 with a catalyst to generate products of ethylene 13. Then, the products of ethylene 13 are transformed into products of olefin 14 having 6~20 carbon atoms ($C_6$~$C_{20}$) through oligomerization 131 with a catalyst. The products of olefin 14 are hydrotreated 141 into products of hydrocarbon of alkane 15 having long carbon chains of $C_6$~$C_{20}$.

(b) The products of lignin 12 are processed through depolymerization/deoxygenation 121 to generate products of aromatic hydrocarbon 16 and processed through gasification 122 to generate products of syngas 17. The products of syngas 17 are processed through a synthesis reaction 171 to generate methanol or dimethyl ether 18 to be dehydrated/aromatized 181 with a catalyst to generate products of aromatic hydrocarbon 16 to be blended into gasoline/jet fuel/diesel. Or, the products of syngas 17 are processed through a water-gas shift reaction 172 to generate hydrogen 19 to be used in hydrogenation reactions of olefins.

Thus, a novel method of transforming biomass into hydrocarbons is obtained.

The non-food biomass is a fiber material or a mixture of fiber materials and the fiber material is straw, bagasse, *miscanthus*, bamboo, hardwood, softwood, sunflower stalk or *Pennisetum*.

On using, the present invention uses a non-food biomass of cellulose and semi-cellulose as a raw material to be transformed for generating alcohol (i.e. ethanol) through fermentation while lignin in the biomass becomes byproduct to be left during processing. Thus, the whole processes are effectively integrated to improve product economy. In FIG. 1, the bio-alcohol (i.e. ethanol) is processed through dehydration with a catalyst to generate ethylene (a conventional reaction, no need to describe in detail). Then, ethylene is transformed into olefins having $C_6$~$C_{20}$ through oligomerization with a catalyst (a conventional reaction, no need to describe in detail). A part of olefins is hydrotreated (a conventional reaction, no need to describe in detail). Thus, hydrocarbons of alkane having $C_6$~$C_{20}$ are generated, each of which has a total olefin content meeting regulations. Therein, hydrocarbons having 6~10 carbon atoms are used as gasoline; hydrocarbons having 8~16 carbon atoms are used as jet fuel; and hydrocarbons having 16~20 carbon atoms are used as diesel.

The lignin left is a by-product of the ethanol production and can be further depolymerized/deoxygenated to generate aromatic hydrocarbons (a conventional reaction, no need to describe in detail); or gasified to produce syngas. Syngas is synthesized into methanol or dimethyl ether to be dehydrated with a zeolite catalyst to generate aromatic hydrocarbons (a conventional reaction, no need to describe in detail). The aromatic hydrocarbons are used to be blended into gasoline/jet fuel/diesel. Or, lignin can be gasified into syngas to be processed through a water-gas shift reaction to generate hydrogen to be used in hydrogenation reactions of olefins. Thus, the integrated biomass refining process enhances product breadth of the whole plant and economy of the production.

In the present invention, selectivity of ethylene is higher than 90%. Ethylene has high reactivity and, by using an acidic catalyst, the length of carbon chain can be lengthened through oligomerization under a mild reaction condition. Meanwhile, lignin can be used to produce hydrogen or aromatic hydrocarbons. As corresponding to the general biomass refinery which uses lignin as a fuel, the present invention further enhances the use of lignin, whose advantages to the products of HEFA (Hydroprocessed Ethers and Fatty Acids) & FT SPK (Fisher-Tropsch Synthetic Paraffinic Kerosene) are shown in Table 1.

TABLE I

|  | FT SPK | HEFA SPK | The present invention |
|---|---|---|---|
| Raw material | Coal, natural gas, biomass | Oily biomass | biomass |
| $C_8$~$C_{16}$ selectivity | ~15% | 25-50% | >60% |

TABLE I-continued

|  | FT SPK | HEFA SPK | The present invention |
|---|---|---|---|
| estimation minimum economic scale estimation | ~400 kiloliters | ~150 kiloliters | ~150 kiloliters |
| Technical features | Having a variety of source material Mature technology Need for mass production Low selectivity, subject to further refinement for enhancing yield of target product Refined products mostly having straight chains | Using biological oily source material only, having great impact on cost Unrefined products with very narrow carbon number distribution | Producing alcohol through fermentation After dehydration, oligomerizing olefin to be saturated through hydrogenation Products containing alkanes/aromatic hydrocarbons if transforming lignin into aromatic hydrocarbons |

To sum up, the present invention is a method of transforming biomass into hydrocarbons, where a second-generation bio-ethanol technology is provided for transforming primary products of ethanol into gasoline/jet fuel/diesel and transforming byproducts of lignin into aromatic hydrocarbons/hydrogen with biomass refining processes integrated to effectively increase product breadth and reduce production cost.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of transforming biomass into hydrocarbons, comprising steps of:
    preprocessing a non-grain biomass and fermenting said biomass into ethanol and lignin;
    processing said ethanol through dehydration with a catalyst to obtain ethylene; transforming said ethylene into olefin having 6~20 carbon atoms through oligomerization with a catalyst; and hydrotreating said olefin into alkanes having long carbon chains of $C_6$~$C_{20}$, wherein said alkanes having 6~10 carbon atoms form gasoline; said alkanes having 8~16 carbon atoms form jet fuel; and said alkanes having 16~20 carbon atoms form diesel fuel;
    processing said lignin through depolymerization/deoxygenation to obtain aromatic hydrocarbon;
    processing said lignin through gasification to obtain syngas; and
    processing said syngas through a synthesis reaction to obtain one or both of methanol and dimethyl ether which is then dehydrated with a catalyst to obtain aromatic hydrocarbon and blended into gasoline/jet fuel/diesel and/or processing the syngas through a water-gas shift reaction to obtain hydrogen which is then used in hydrogenation reactions of olefins.

2. The method according to claim 1, wherein said non-grain biomass is selected from a group consist of a fiber material and a mixture of fiber materials and said fiber material is selected from a group consist of straw, bagasse, *miscanthus*, bamboo, hardwood, softwood, sunflower stalk and *Pennisetum*.

3. The method according to claim 1, wherein a selectivity of said ethylene is higher than 90%.

4. The method according to claim 1, comprising using an acidic catalyst to process said oligomerization of ethylene to lengthen carbon chains.

5. The method according to claim 1, wherein a selectivity of said hydrocarbon having 6~10 carbon atoms is greater than 60%.

* * * * *